United States Patent [19]

Koga et al.

[11] Patent Number: 4,883,912

[45] Date of Patent: Nov. 28, 1989

[54] PROCESS FOR THE RECOVERY OF ACETIC ACID

[75] Inventors: Kunio Koga; Koji Shima; Mutsumi Samejima, all of Himeji, Japan

[73] Assignee: Daicel Chemical Industries, Ltd., Sakai, Japan

[21] Appl. No.: 865,927

[22] Filed: May 14, 1986

Related U.S. Application Data

[63] Continuation of Ser. No. 576,282, filed as PCT JP83/00216 on Jul. 6, 1983, published as WO84/00364 on Feb. 2, 1984, abandoned.

[30] Foreign Application Priority Data

Jul. 6, 1982 [JP] Japan .................................. 57-117445
Jul. 6, 1983 [WO] PCT Int'l Appl. ... PCT/JP83/00216

[51] Int. Cl.$^4$ ...................... C07C 51/48; C07C 51/50; C07C 53/08
[52] U.S. Cl. ..................................... 562/608; 203/16; 203/44; 203/59; 562/513
[58] Field of Search ............................... 562/608, 513

[56] References Cited

U.S. PATENT DOCUMENTS 4,353,784 10/1982 Koga et al. ........................... 203/16

FOREIGN PATENT DOCUMENTS 56-10131 2/1981 Japan .................................... 562/608
57-24324 2/1982 Japan .................................... 562/608

OTHER PUBLICATIONS

Fieser et al., Organic Chemistry, D. C. Heath & Co., Boston, 1944, p. 228.

*Primary Examiner*—Vivian Garner
*Attorney, Agent, or Firm*—Flynn, Thiel, Bouteil & Tannis

[57] ABSTRACT

In a process for the recovery of acetic acid by extracting acetic acid from an aqueous acetic acid solution containing a metallic salt of sulfuric acid with an organic extractant comprising a tertiary amine and an organic diluent and recovering acetic acid from the liquid extract, a mixture of a tertiary amine containing sulfuric acid and an organic diluent is used as an organic extractant so as to suppress energy consumption and to increase extraction efficiency.

7 Claims, No Drawings

PROCESS FOR THE RECOVERY OF ACETIC ACID

This application is a continuation of U.S. Ser. No. 576,282, filed as PCT JP83/00216 on Jul. 6, 1983, published as WO84/00364 on Feb. 2, 1984, now abandoned.

TECHNICAL FIELD

The present invention is related to a process for the recovery of acetic acid from an aqueous acetic acid solution containing a metallic salt of sulfuric acid, more particularly, to an improvement in the process for the extraction of acetic acid from an aqueous acetic acid solution with an organic extractant.

BACKGROUND ART

An aqueous acetic acid solution discharged from the process for the preparation of cellulose acetate contains metallic salts of sulfuric acid, such as Na, K, Ca, Mg, Fe, Al, or Zn sulfate formed by the neutralization of sulfuric acid used as catalyst in the acetylation process (refer to the Japanese Patent Publication No. 17580/1973). Magnesium sulfate, for example, is contained in a concentration not higher than the saturation solubility. Acetic acid has been recovered from this aqueous solution by extraction with ethyl acetate or other organic solvents. In this method, the extraction is not affected by the metallic salts of sulfuric acid contained in the aqueous acetic acid solution, but the method in which an organic solvent such as ethyl acetate is used as an extractant is not fully satisfactory from the viewpoint of the extraction efficiency or energy consumption, because the distribution coefficient of acetic acid is small in general. The efficiency of recovery by extraction is much dependent on the distribution coefficient, and a large amount of solvent must be used to raise the extraction ratio, which results disadvantageously in large energy consumption in the process of separation.

The inventors proposed a process for the extraction of acetic acid from an aqueous solution using an organic solvent containing a tertiary amine as an extractant (refer to the Japanese Patent Laid-Open No. 10131/1981) which is an excellent extractant for the extraction of acetic acid. As a result of further studies of the inventors, however, it was found that in case an organic extractant containing a tertiary amine is used for an aqueous acetic acid solution containing a metallic salt of sulfuric acid, an amine salt of acetic acid reacts with the metallic salt of sulfuric acid in an extractor so that acetic acid is dissolved in the form of a metallic salt in the raffinate, and the extraction efficiency is lowered because of this unrecovered acetic acid.

DISCLOSURE OF INVENTION

An object of the present invention is to establish a method of extracting acetic acid with a high efficiency and small energy consumption for the recovery of acetic acid from an aqueous acetic acid solution containing metallic salts of sulfuric acid. The present invention has enabled acetic acid to be extracted with an amine, wherein the disadvantages of the conventional method are overcome.

More particularly, the inventors have found as a result of studies that the extraction efficiency is improved, with no loss of acetic acid, by using an organic extractant containing a tertiary amine, in which a small amount of sulfuric acid is contained, for the extraction of acetic acid from an aqueous acetic acid solution containing metallic salts of sulfuric acid. The amount of sulfuric acid in the extractant must be at least equimolar with that of the metallic salt of sulfuric acid in the aqueous acetic acid solution, but too much sulfuric acid is liable to reduce the distribution coefficient of acetic acid. As a result of the investigation by the present inventors, the amount of sulfuric acid in the recycle organic extractant is within the range of 1 to 6 mol, preferably from 1.5 to 4 mol per mol of the metallic salt of sulfuric acid in the aqueous acetic acid solution, and at the same time the recommendable sulfuric acid concentration is not higher than 5 percent by weight. The above-mentioned extractant is brought into countercurrent contact with the aqueous acetic acid solution containing metallic salts of sulfuric acid in multiple stages for the extraction of acetic acid.

In the method of the present invention, the metallic salts of sulfuric acid contained in the aqueous acetic acid solution come into contact with an amine salt of acetic acid at around the inlet of an extractor, where acetic acid is highly concentrated, to form metallic salts of acetic acid. These metallic salts are dissolved in the water phase, while sulfuric acid is dissolved in the solvent phase. However, the metallic salts of acetic acid, in countercurrent contact with sulfuric acid in the extractant, again react with sulfuric acid in the extractant at around the outlet of the extractor, where the concentration of acetic acid is low, to form metallic salts of sulfuric acid to be dissolved in the water phase, and discharged out of the system. The loss of acetic acid is thus completely prevented. Though sulfuric acid contained in the extractant is exchanged with the sulfate group contained in the aqueous acetic acid solution in the extractor, it is not necessary to make up sulfuric acid since the extractant is recycled. It is recommendable to admix a predetermined amount of sulfuric acid with the initially or subsequently supplied extractant. If sulfuric acid is not incorporated, acetic acid will be lost until the sulfuric acid concentration in the extractant becomes steady.

The sulfuric acid concentration in the recycle extractant is not increased when acetic acid is satisfactorily extracted from the aqueous acetic acid solution. When the extraction is insufficient because of some troubles in the extraction process, however, the acetic acid concentration at around the outlet of the extractor is increased so that the metallic salts of acetic acid are not completely reconverted into the metallic salts of sulfuric acid, resulting in an increase in the sulfuric acid concentration in the extractant. The performance of the extractant is lowered with increasing sulfuric acid concentration in the extractant, resulting in more and more increase in the sulfuric acid concentration in the extractant. The recycle extractant, therefore, must be controlled to prevent too much increase in the sulfuric acid concentration.

This control can be achieved by bringing an aqueous solution of alkali such as sodium hydroxide into contact with the extractant, but this method is not recommendable because the extractant is likely to form an emulsion and to be transferred to the washing liquid in vain. Alternatively, the sulfuric acid concentration in the extractant can be controlled by bringing the extractant into contact with an aqueous solution of an appropriate concentration containing metallic salts of acetic acid to lower the sulfuric acid concentration without difficulties in liquid separation caused by the emulsification of the extractant. Moreover, this method permits the control to be performed merely by charging an aqueous solution containing metallic salts of acetic acid into the extractor at around its entrance. The metallic salts of acetic acid then react with sulfuric acid in the extracted solution to form metallic salts of sulfuric acid, and the remaining acetic acid is recovered. The sulfuric acid concentration in the extractant is thus very advantageously controlled in the process for the recovery of acetic acid from the aqueous acetic acid solution containing metallic salts of sulfuric acid.

The organic extractant containing a tertiary amine according to the present invention is preferably a combination of a tertiary amine with an oxygen-containing organic solvent, as described in the above-mentioned Japanese Patent Laid-Open No. 10131/1981.

The present invention will now be described in more detail by the best mode for carrying out the invention: acetic acid is extracted from the aqueous solution using, as an organic extractant, a mixture of a tertiary amine such as tri-n-octylamine (TOA) and an oxygen-containing organic solvent such as 3,3,5-trimethylcyclohexanone (TMCH) (both have boiling points higher than that of acetic acid) in an extractor devised to increase the dispersion/coalescence frequency of droplets, for example, a mixer-settler extractor. The obtained liquid extract is first freed of water which has been contained in the extract in a small amount in a dehydration/distillation column, and then introduced into an acetic acid recovery column, where acetic acid free of water is obtained from the top of the column and the regenerated extractant from the bottom. The separation of acetic acid from the extractant is smoothly effected by maintaining a temperature at the bottom of the column at around, for example, 140° to 150° C. Steam is utilized as the source of this heating as usual in chemical factories. Part of the regenerated extractant obtained from the bottom is introduced into the top of the dehydration/distillation column to be used as a reflux liquid therein. Although acetic acid is usually likely to go up in the column with water and the oxygen-containing compounds, it is extracted by the reflux liquid containing a tertiary amine and goes down, preventing the effusion of acetic acid out of the dehydration/distillation column. The remainder of the regenerated extractant (e.g. TOA and TMCH) obtained from the bottom of the acetic acid recovery column is recycled to the extractor of the first step.

The tertiary amines to be used are preferably those having a boiling point higher than that of acetic acid and form a non-aqueous phase. The number of carbon atoms contained in the tertiary amine should be around 12 to 40, considering the low solubility in the water phase and the separability from acetic acid by distillation. It is also preferable in order to obtain a large apparent distribution coefficient that the tertiary amine has no large branches near the nitrogen atom. It is undesirable to have an ethyl or larger substituent group on a carbon atom neighboring the nitrogen atom by interposing one $CH_2$, not to mention adjacent to the nitrogen atom. It is also to be avoided to have a benzyl group or those having a cyclic structure near the nitrogen atom. In other words, the tertiary amines should be selected, from those which have a partial structure represented by $>N-CH_2-CR^1R^2$, wherein $R^1$ is a hydrogen atom and $R^2$ is a hydrogen atom or a methyl group, for example, $C_6$ or higher trialkylamines such as trihexylamine, trioctylamine, triisooctylamine (tris-2,4,4-trimethylpentylamine), trilaurylamine, dimethyllaurylamine, dimethylhexadecylamine, methyldi(tridecyl)amine, or dimethyldecylamine; tertiary amines having an alkenyl group such as dimethyloleylamine or butylbis(5,5,7,7-tetramethyl-oct-2-en-1-yl)amine (XE-204); or teritary amine mixtures such as dimethylcocoamine, dimethyl(-$C_{8-12}$ alkyl)amines, or dimethyl(hydrogenated tallow)amine. Commercially available tertiary amines can be used as such. It is also possible to obtain tertiary amines by alkylating primary or secondary amines available as intermediates by a known method. Among many usable tertiary amines mentioned above, TOA is readily available and shows an excellent apparent partition coefficient when it is admixed with an oxygen-containing organic solvent to form an extractant.

Examples of the organic solvent to be used in combination with the amines are those oxygen-containing organic solvents which have a boiling point higher than acetic acid, e.g. ketones, alcohols, carboxylic esters, or phosphoric esters. When these solvents are used in combination with the tertiary amines described above, acetic acid in the aqueous solution can be extracted with a particularly large apparent distribution coefficient.

EXAMPLE 1

A 27.6 wt% aqueous acetic acid solution containing 0.67 wt% of magnesium sulfate was charged into the first vessel at 420 g/H (0.023 mol/H in terms of magnesium sulfate) at 30° C., using a countercurrent five-stage mixer-settler extractor made of glass. An organic extractant comprising a mixed solvent of tri-n-octylamine and 3,3,5-trimethylcyclohexanone in a volume ratio of 50:50, wherein 1.1 wt% of sulfuric acid had been incorporated, was charged countercurrently from the fifth vessel at 422 g/H (0.047 mol/H in terms of sulfuric acid).

As a result, the liquid extraction waste was discharged at 277 g/H, in which 0.96 wt% (0.22 mol/H) of magnesium sulfate was contained. Magnesium acetate was not detected. The amount of acetic acid in the liquid waste was 0.07 wt%, that is, almost all of acetic acid was extracted. The liquid extract was discharged at 558 g/H in which 0.82 wt% (0.047 mol/H) of sulfuric acid was contained.

COMPARATIVE EXAMPLE 1

A 27.6 wt% aqueous acetic acid solution containing 0.67 wt% of magnesium sulfate was charged into the first vessel at 400 g/H (0.022 mol/H in terms of magnesium sulfate) at 30° C., using the same equipment as used in Example 1, and an organic extractant containing 50 vol% of the same tertiary amine as used in Example 1 was countercurrently charged from the fifth vessel at 408 g/H.

As a result, the liquid extraction waste was discharged at 264 g/H, wherein 90 ppm (0.0002 mol/H) of magnesium sulfate was found. Magnesium acetate was contained in an amount of 0.79 wt% (0.015 mol/H). The liquid extract was discharged at 534 g/H, in which 0.55 wt% (0.030 mol/H) of sulfuric acid was accumulated. The result shows that acetic acid has been lost in the liquid extraction waste in the form of magnesium acetate. It will be understood that the result is much worse than that of Example 1.

EXAMPLE 2

A 27.6 wt% aqueous acetic acid solution containing 0.67 wt% of magnesium sulfate was charged at 400 g/H (0.022 mol/H in terms of magnesium sulfate) and a 26 wt% aqueous magnesium acetate solution at 70 g/H (0.13 mol/H in terms of magnesium acetate) into the first vessel at 30° C., using the same equipment as used in Example 1, and an organic extractant containing 50 vol% of the same tertiary amine as used in Example 1, wherein 5.3 wt% of sulfuric acid had been incorporated, was charged countercurrently from the fifth vessel at 402 g/H (0.22 mol/H in terms of sulfuric acid).

As a result, the liquid extraction waste was discharged at 330 g/H, in which 5.4 wt% (0.15 mol/H) of magnesium sulfate was contained, but no magnesium acetate was detected. The liquid extract was discharged at 540 g/H, the sulfuric acid concentration of which was 1.63 wt% (0.09 mol/H). It has thus been shown that the sulfuric acid concentration in the recycle extractant can be controlled at 5% or less by using an aqueous magnesium acetate solution.

Acetic acid can be recovered from the liquid extract obtained by the present invention by a known method such as distillation.

What is claimed is:

1. A process for recovering acetic acid from an aqueous acetic acid solution containing one or more metal salts of sulfuric acid as an impurity, which comprises the steps of:

performing liquid-liquid extraction by flowing said aqueous acetic acid solution countercurrent to an organic liquid extractant consisting essentially of a mixture of a tertiary amine, an oxygen-containing organic solvent and sulfuric acid through a plurality of mixer-settler stages, the amount of sulfuric acid in said organic liquid extractant being at least equimolar to the amount of said metal salt of sulfuric acid in said aqueous acetic acid solution so that said amine reacts with the acetic acid to form an amine salt and said metal salt of sulfuric acid contacts and reacts with the amine salt of acetic acid in a zone containing a high concentration of acetic acid to form a metal salt of acetic acid which is dissolved in the aqueous phase, and then the metal salt of acetic acid reacts with sulfuric acid in a zone containing a low concentration of acetic acid to form a metal salt of sulfuric acid which is dissolved in the aqueous phase and the acetic acid is dissolved in the organic phase; and then separating and recovering the acetic acid from the organic liquid extractant.

2. A process as claimed in claim 1 in which the amount of sulfuric acid in said organic liquid extractant is from 1 to 6 mols per mol of said metal salt of sulfuric acid in said aqueous acetic acid solution.

3. A process as claimed in claim 1 in which the amount of sulfuric acid in said organic liquid extractant is from 1.5 to 4.0 mols per mole of said metal salt of sulfuric acid in said aqueous acetic acid solution, and the concentration of sulfuric acid in said organic liquid extractant is not higher than 5 percent by weight.

4. A process as claimed in claim 1 in which said tertiary amine and said oxygen-containing organic solvent have boiling points higher than the boiling point of acetic acid.

5. A process as claimed in claim 4 in which said tertiary amine has from 12 to 40 carbon atoms.

6. A process as claimed in claim 4 in which said tertiary amine is selected from the group consisting of trihexylamine, trioctylamine, triisooctylamine, trilaurylamine, dimethyllaurylamine, dimethylhexadecylamine, methyldi(tridecyl)amine, dimethyladecylamine, dimethyloleylamine, butylbis(5,5,7,7-tetramethyl-oct-2-en-1-yl)amine, dimethyl cocoamine, dimethyl ($C_{8-12}$alkyl)amines and dimethyl(hydrogenated tallow)amine, and said oxygen-containing organic solvent is selected from the group consisting of ketones, alcohols, carboxylic esters and phosphoric esters.

7. A process for recovering acetic acid from an aqueous acetic acid solution containing one or more metal salts of sulfuric acid as an impurity, which comprises the steps of:

performing countercurrent liquid-liquid extraction by flowing in opposite directions through a mixer-settler extraction system, (1) said aqueous acetic acid solution and (2) an organic liquid extractant consisting essentially of a mixture of a tertiary amine, an oxygen-containing organic solvent and sulfuric acid wherein said tertiary amine and said oxygen-containing organic solvent have boiling points higher than the boiling point of acetic acid, the concentration of sulfuric acid in said organic liquid extractant is not higher than 5 percent by weight and the amount of sulfuric acid in said extractant is from 1.5 to 4.0 mols per mol of said metal salt of sulfuric acid in said aqueous acetic acid solution, so that said amine reacts with the acetic acid to form an amine salt, said metal salt of sulfuric acid contacts and reacts with the amine salt of acetic acid in a zone containing a high concentration of acetic acid to form a metal salt of acetic acid which is dissolved in the aqueous phase, and then the metal salt of acetic acid reacts with sulfuric acid in a zone containing a low concentration of acetic acid to form a metal salt of sulfuric acid which is dissolved in the aqueous phase and the acetic acid is dissolved in the organic phase; and then separating and recovering the acetic acid from the organic liquid extractant.

* * * * *